United States Patent [19]
Grendahl

[11] Patent Number: 4,759,762
[45] Date of Patent: Jul. 26, 1988

[54] ACCOMMODATING LENS

[76] Inventor: Dennis T. Grendahl, 2070 Shoreline Dr., Orono, Minn. 55391

[21] Appl. No.: 62,572

[22] Filed: Jun. 16, 1987

Related U.S. Application Data

[63] Continuation of Ser. No. 709,807, Mar. 8, 1985, abandoned.

[51] Int. Cl.⁴ .............................................. A61F 2/16
[52] U.S. Cl. ...................................... 623/6; 351/161; 351/162; 351/172
[58] Field of Search ................... 623/6; 351/160, 161, 351/162, 168, 172

[56] References Cited

U.S. PATENT DOCUMENTS

| | | | |
|---|---|---|---|
| 3,034,403 | 5/1962 | Neefe | 351/162 |
| 3,037,425 | 6/1962 | De Carle | 351/161 |
| 3,339,997 | 9/1967 | Wesley | 351/161 |
| 3,454,332 | 7/1969 | Siegel | 351/162 |
| 4,402,579 | 9/1983 | Poler | 623/6 X |
| 4,435,856 | 3/1984 | L'Esperance | 623/6 |
| 4,605,409 | 8/1986 | Kelman | 623/6 |

FOREIGN PATENT DOCUMENTS 35177  1/1965  German Democratic Rep. .................... 351/162

OTHER PUBLICATIONS

Americal IOL International Intraocular Lenses, Style 115, Style 100, Style 130 & 130A Lenses (1 page advertisement), Dec. 29, 1981.

Primary Examiner—Ronald L. Frinks
Attorney, Agent, or Firm—Hugh D. Jaeger

[57] ABSTRACT

An accommodating lens including a lens optic with two indexes of refraction, the indexes of refraction based on dual cylindrical materials of the lens optic or a dual composite material of the lens optic. The dual cylindrical material or dual composite material of the lens optic is of PMMA. The lens can be either a posterior chamber lens or an anterior chamber lens, and include a plurality of outwardly extending loops.

4 Claims, 6 Drawing Sheets

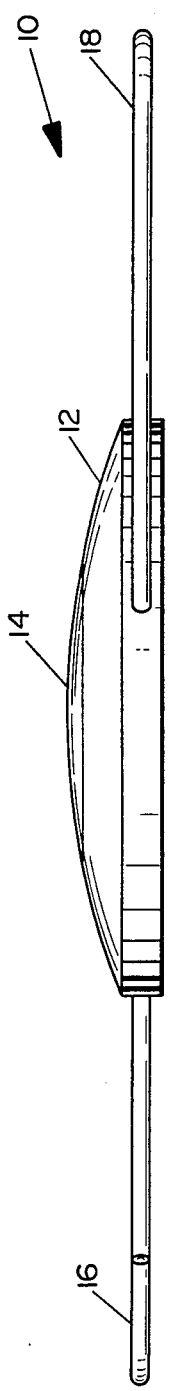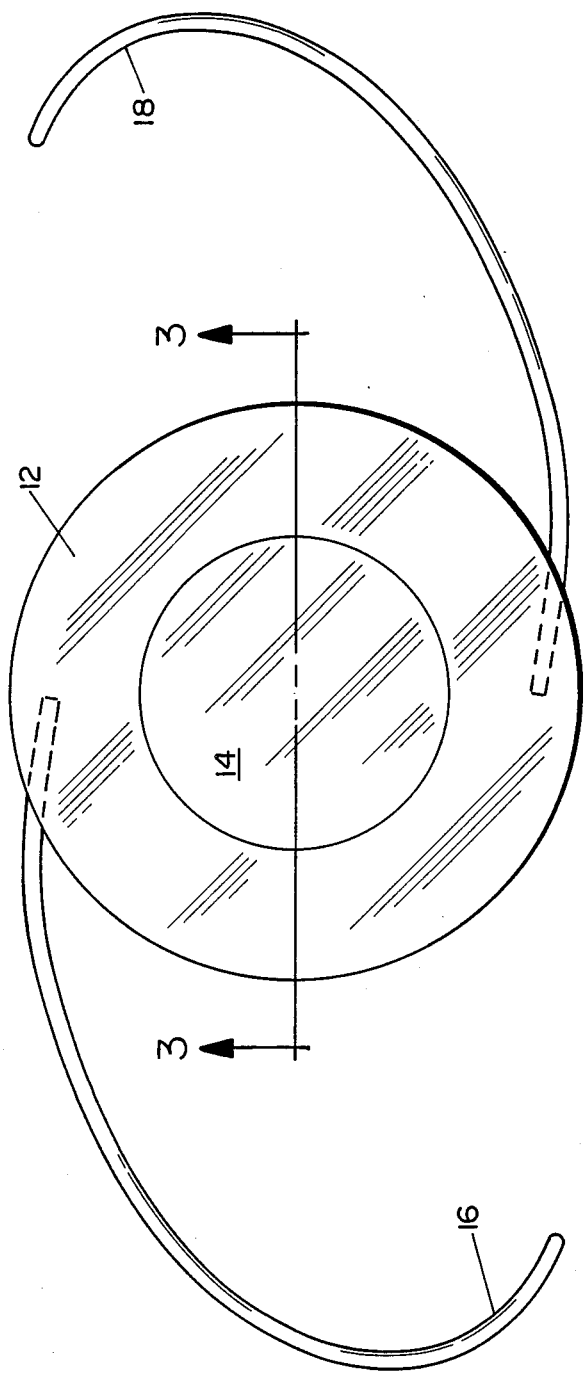
FIG. 1
FIG. 2

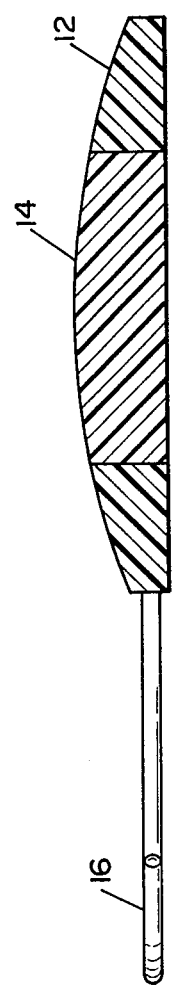
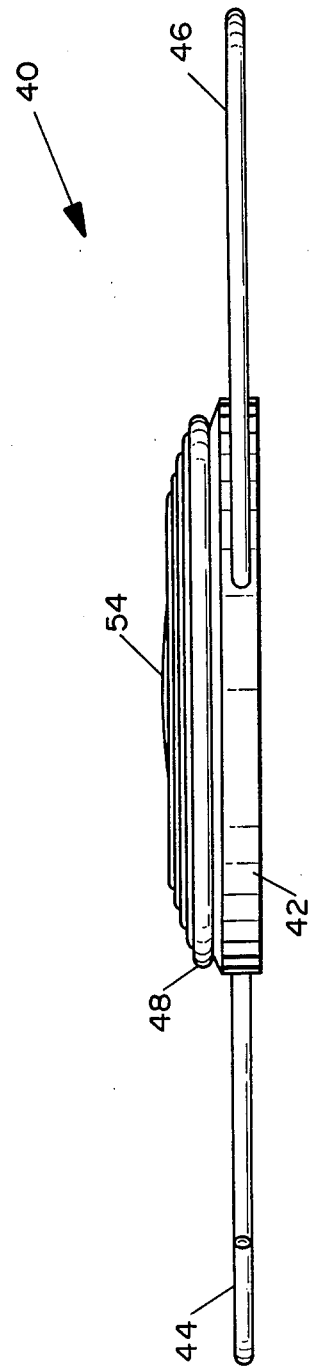

ACCOMMODATING LENS

CROSS REFERENCE TO CO-PENDING APPLICATIONS

This application is a continuation of application Ser. No. 709,807, filed Mar. 8, 1985, and now abandoned.

BACKGROUND OF THE INVENTION

1. Field of the Invention

The present invention pertains to an intraocular lens, and more particularly, pertains to an accommodating lens for either the posterior or the anterior chamber of the eye.

2. Description of the Prior Art

There have been different methods used to change the diopter power of a lens in the human eye. The first is mechanical by creating a soft material lens where the power is changed by shape. The second is changing location of the lens along the optical axis, although, this has not been advanced for implant in the human eye. The third is an extremely advanced method under experimentation of using a grid effect caused by polarized liquid crystals changing the index of refraction of the media. A fourth has been using a small aperture to increase the depth of field, which is the subject matter of the present invention.

Mechanical attachments to prior art lenses have been ineffective as the attachments would not be secure and there was lack of any clinical experience between the lenses and the muscles.

The present invention overcomes the disadvantages of the prior art by providing an aperture type lens made from either dual cylindrical materials or dual composite materials forming the lens where the iris acts as the f stop.

SUMMARY OF THE INVENTION

The general purpose of the present invention is to provide an accommodating lens of a dual cylindrical material or a dual composite material providing an aperture to increase the depth of field. The lens can be either for the posterior chamber or the anterior chamber of the eye.

According to one embodiment of the present invention, there is provided an accommodating lens including a dual cylindrical member lens optic providing for depth of the aperture field.

According to another embodiment of the present invention, there is provided an intraocular lens including a lens optic and a length of PMMA monofilament wound about a posterior or anterior surface of the lens towards the center of the lens. The length of PMMA optic can be wound around either the posterior surface or the anterior surface of the lens optic.

One significant aspect and feature of the present invention is an accommodating intraocular lens with a dual index of refraction and small aperture to increase depth of field.

Another significant aspect and feature of the present invention is an accommodating lens of PMMA material which is well recognized by the Food & Drug Administration as being acceptable for implant in the human eye.

Having thus described embodiments of the present invention, it is the principal object hereof to provide an accommodating lens.

One object of the present invention is to provide an accommodating lens which is implantable in either the posterior chamber or the anterior chamber of the eye.

Another object of the present invention is to provide an accommodating lens which is entirely composed of PMMA material.

BRIEF DESCRIPTION OF THE DRAWINGS

FIG. 1 illustrates a side view of an accommodating lens of a dual cylindrical material;

FIG. 2 illustrates a top view of FIG. 1;

FIG. 3 illustrates a cross-sectional view of FIG. 2 taken along line 3—3;

FIG. 4 illustrates a side view of an accommodating lens of dual composite material;

DESCRIPTION OF THE PREFERRED EMBODIMENTS

Figure 5:
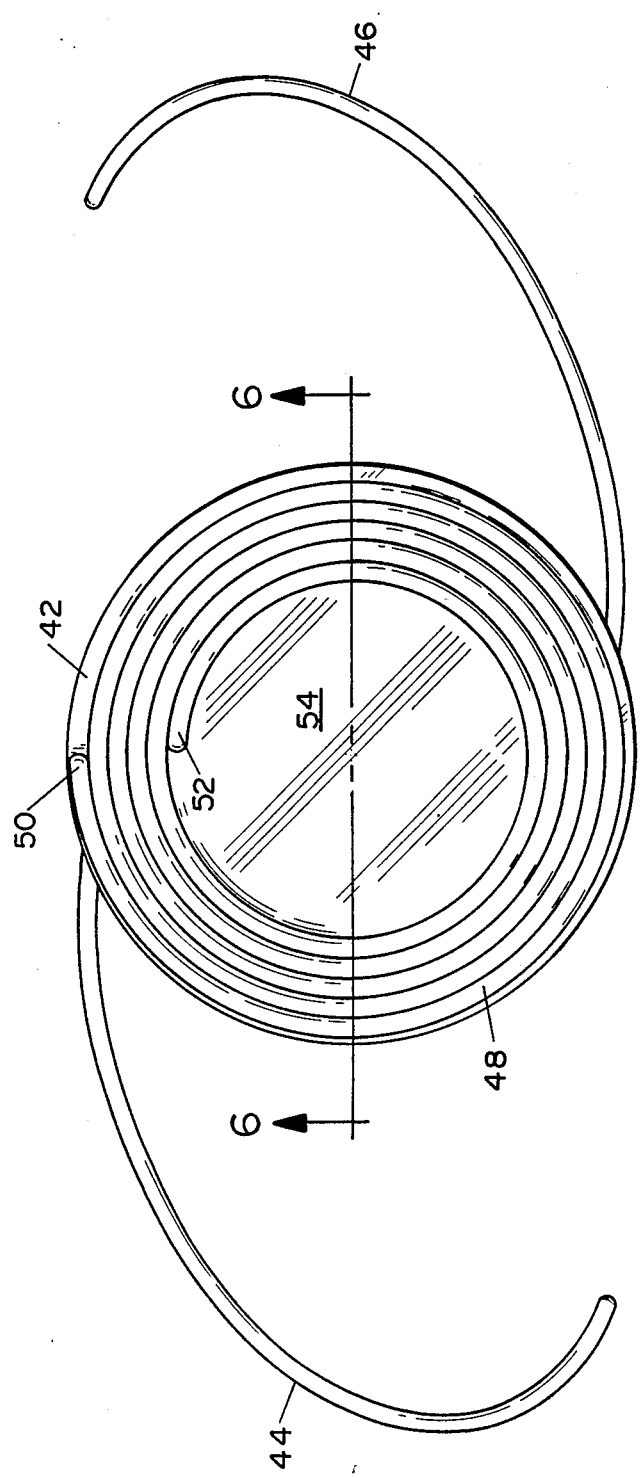
FIG. 5 illustrates a top view of FIG. 4.

FIG. 1 illustrates a side view of an accommodating intraocular lens 10 including dual cylindrical members 12 and 14 forming the lens optic, and outwardly extending loops 16 and 18. Each of the loops assumes a configuration similar to that denoted as a Lindstrom lens, Style 20, sold by the assignee of the present invention. The members 12-18 are made out of PMMA, polyethylmethacrylate. The ends of the loops are secured into the member 12.

FIG. 2 illustrates a top view of FIG. 1 where all numerals correspond to those elements previously described.

FIG. 3 illustrates a cross-sectional view of FIG. 2 taken along line 3—3, where all numerals correspond to those elements previously described.

MODE OF OPERATION

The dual cylindrical members 12 and 14 provide a dual index of refraction thereby providing a smaller aperture for increasing the depth of field. The depth of field is provided by the aperture difference between members 12 and 14, especially where member 12 could be blue PMMA, while member 14 could be clear PMMA.

FIG. 4 illustrates a side view of an accommodating lens 40 including a lens optic 42, loops 44 and 46, and a length of PMMA monofilament 48 wound from a first point 50 to an end point 52 of FIG. 5, creating an aperture area 54.

FIG. 5 illustrates a top view of FIG. 4 where all numerals correspond to those elements previously described. Particularly illustrated is the aperture area 54.

Figure 6:
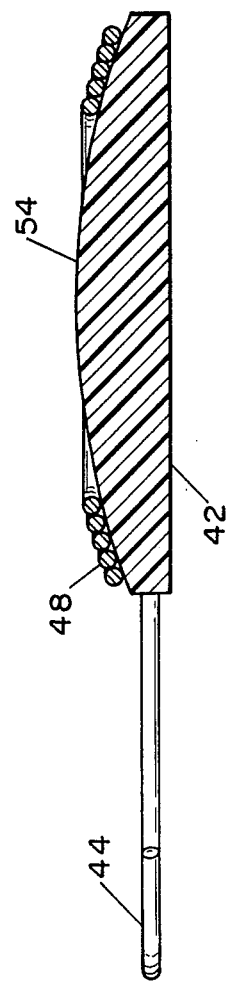
FIG. 6 illustrates a cross-sectional view of FIG. 5 taken along line 6—6.

FIG. 6 illustrates a cross-sectional view of FIG. 5 taken along line 6—6, where all numerals correspond to those elements previously described.

MODE OF OPERATION

The aperture area is created by the dual composite material of the monofilament 48 about the lens optic 42, creating the aperture area 54 which creates an aperture to increase the depth of field.

ALTERNATIVE EMBODIMENT

Figure 7:
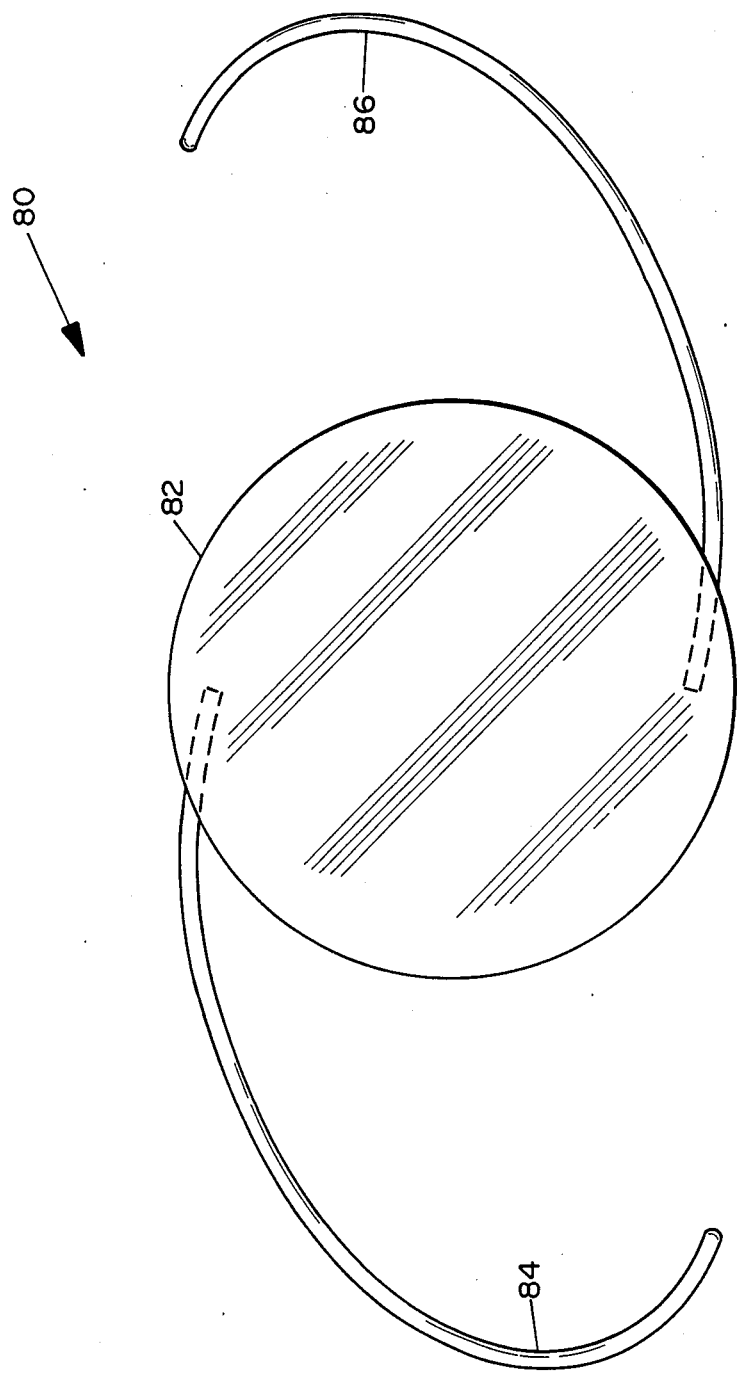
FIG. 7 illustrates a top view of an accommodating lens of dual composite material, an alternative embodiment.

FIG. 7 illustrates a top view of an accommodating lens 80 including a lens optic 82, and loops 84 and 86.

Figure 8:
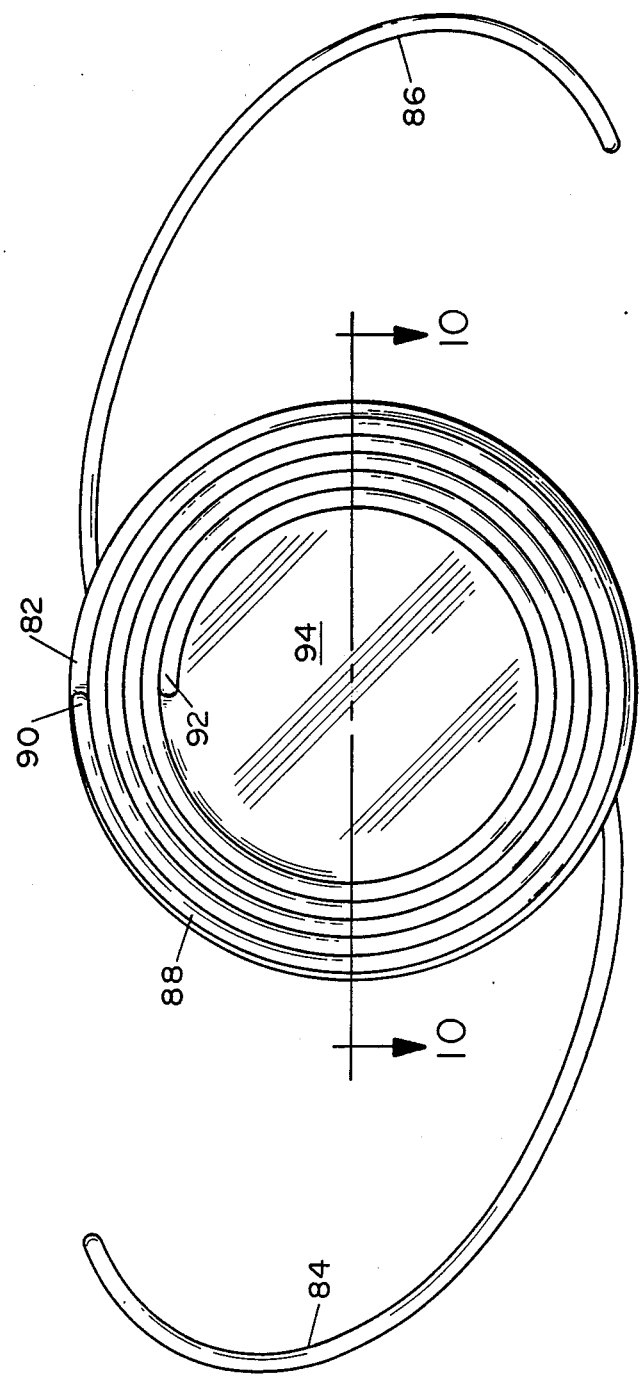
FIG. 8 illustrates a bottom view of FIG. 7.

FIG. 8 illustrates a bottom view of FIG. 7 where all numerals correspond to those elements previously described including a length of monofilament material 88 with starting point 90 and ending at 92, creating an aperture 94.

Figure 9:
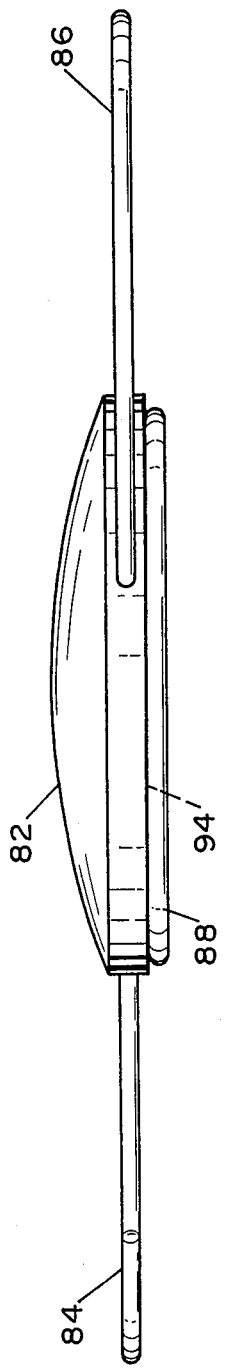
FIG. 9 illustrates a side view of FIGS. 7 and 8.

FIG. 9 illustrates a side view of FIGS. 7 and 8 where all numerals correspond to those elements previously described.

Figure 10:
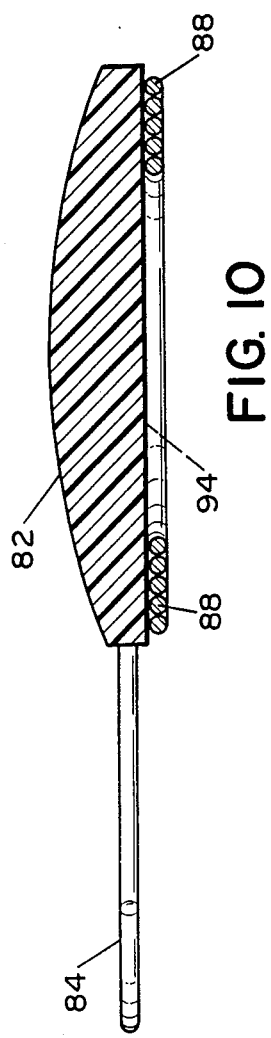
FIG. 10 illustrates a cross-sectional view of FIG. 8 taken along line 10—10.

FIG. 10 illustrates a cross-sectional view of FIG. 8 taken along line 10—10, where all numerals correspond to those elements previously described.

MODE OF OPERATION

The lens 80 of FIGS. 7-10 corresponds in like operation to the accommodating lens of FIGS. 1-3 and FIGS. 4-6.

I claim:

1. An intraocular lens comprising:
   a. an optic composed of two rigid, transparent elements having different indices of refraction which provide an aperture difference for increasing the depth of field of said optic, one element is the lens itself and the other element is a length of monofilament spirally wound on the surface of the lens to create an aperture; and,
   b. a plurality of loops extending outwardly from said optic.

2. The lens of claim 1 in which the elements are concentric cylinders.

3. The lens of claim 2 in which the elements are of different colors.

4. A lens according to anyone of the preceding claims composed of PMMA.

* * * * *